United States Patent
Facklam

(10) Patent No.: US 9,080,032 B2
(45) Date of Patent: Jul. 14, 2015

(54) MIXED ALKYL BENZYL ESTERS OF SUCCINIC ACID USED AS PLASTICIZERS

(71) Applicants: LANXESS Deutschland GmbH, Cologne (DE); Bioamber International S.A.R.L., Luxembourg (LU)

(72) Inventor: Thomas Facklam, Leverkusen (DE)

(73) Assignees: LANXESS Deutschland GmbH, Cologne (DE); BioAmber International S.A.R.L., Luxembourg (LU)

( * ) Notice: Subject to any disclaimer, the term of this patent is extended or adjusted under 35 U.S.C. 154(b) by 0 days.

(21) Appl. No.: 14/380,415

(22) PCT Filed: Feb. 20, 2013

(86) PCT No.: PCT/EP2013/053382
§ 371 (c)(1),
(2) Date: Aug. 22, 2014

(87) PCT Pub. No.: WO2013/124318
PCT Pub. Date: Aug. 29, 2013

(65) Prior Publication Data
US 2015/0114263 A1 Apr. 30, 2015

(30) Foreign Application Priority Data
Feb. 24, 2012 (EP) .................................. 12156807

(51) Int. Cl.
*C07C 69/40* (2006.01)
*C08K 5/11* (2006.01)
*C09D 7/12* (2006.01)
*C09J 11/06* (2006.01)
*C07C 69/612* (2006.01)

(52) U.S. Cl.
CPC . *C08K 5/11* (2013.01); *C07C 69/40* (2013.01); *C07C 69/612* (2013.01); *C09D 7/1233* (2013.01); *C09J 11/06* (2013.01)

(58) Field of Classification Search
CPC .................................. C07C 69/40; C08K 5/11
USPC ............................ 560/190; 524/314; 106/499
See application file for complete search history.

(56) References Cited

U.S. PATENT DOCUMENTS

2008/0004387 A1  1/2008  Weiss et al.

FOREIGN PATENT DOCUMENTS

DE  1962500 U  6/1967
FR  2026170 A1  9/1970

OTHER PUBLICATIONS

Werpy, T., Petersen, G., et al. in Top Value added Chemicals from Biomass, vol. 1: Results of screening for potential candidates from sugars and synthesis gas, p. 1, Aug. 2004.
Lecaptain et al. in Polym. Bull (2010), 65:589-598 in the paper "Poly(Vinyl Chloride) plasticized with succinate esters: synthesis and characterization".
International Search Report from co-pending Application PCT/EP2013/053382 dated Apr. 30, 2013 2 pages.

*Primary Examiner* — Sikarl Witherspoon

(57) ABSTRACT

The present invention relates to novel succinic acid ester mixtures and to the use thereof as plasticizers for plastic materials. The claimed mixtures are characterized by having good plasticizing effects with low dissolution temperatures.

13 Claims, No Drawings

MIXED ALKYL BENZYL ESTERS OF SUCCINIC ACID USED AS PLASTICIZERS

The present invention relates to novel mixtures of succinic esters based on alkyl and benzyl alcohols, and to use thereof as plasticizers for plastics.

For decades now, plasticizers have been used for the processing of plastics such as polyvinyl chloride (PVC). Plasticizers are additives which are used in polymer processing and which improve processability, flexibility, and extensibility. Since the plasticizers lack any strong bonding to the polymer, they can migrate or evaporate. The plasticizers mainly used for the production of plasticized PVC are phthalic esters such as the all-purpose products di-2-ethylhexyl phthalate (DEHP), diisononyl phthalate (DINP), and diisodecyl phthalate (DIDP). In order to improve processing methods in respect of speed or energy-saving, rapid-gelling plasticizers maybe added, examples being the short-chain phthalates dibutyl phthalate (DBP), diisobutyl phthalate (DiBP), and benzyl butyl phthalate (BBP).

The use of phthalates is subject to ever stricter limitations related to legislation. One example is the banning of, and the restriction of use of, some phthalates in the production of toys and baby products (Directive 2005/84/EC of the European Parliament and of the Counsel of Dec. 14, 2005). The European Chemicals Agency (ECHA) has also included a number of phthalates in the list of candidates for substances of very high concern (SVHC).

Another factor is that the phthalate plasticizers are based on petrochemical feedstocks. Their production releases greenhouse gases, and thus poses a number of problems.

There is therefore a requirement for phthalate-free plasticizers for plastics. Interest here is focused on plasticizers based on renewable raw materials, as a result of issues relating to climate, sustainability, and restricted availability of fossil-derived feedstocks. Plasticizers based on succinic acid could meet these requirements.

Relatively recent developments in the field of "green" technologies have provided an inexpensive and effective route to biobased succinic acid, and it has therefore become possible to use biobased succinic acid on an industrial scale for the production of plasticizers. In this connection, succinic acid has been identified as one of 12 highest-value sugar-based building blocks for syntheses (cf. for example T. Werpy and G. Petersen et al. in Top Value Added Chemicals From Biomass, Volume I: Results of Screening for Potential Candidates from Sugars and Synthesis Gas, page 1)

The use of succinic esters as plasticizers for plastics has been known for quite some time: by way of example DE-A 1962500 describes the use of dialkyl succinates, in particular of dicapryl succinate, as plasticizers for PVC foils resistant to staining.

The use of esters of succinic acid as plasticizers for PVC is described by LeCaptain et al. in Polym. Bull. (2010) 65:589-598 in the paper "Poly(vinyl chloride) plasticized with succinate esters: synthesis and characterization". That document describes dioctyl succinate (DOS), dihexyl succinates (DHS), dibutyl succinates (DBS), and diethyl succinates (DES). Infrared (IR)-, differential scanning calorimetry (DSC)-, and dynamic-mechanical analysis (DMA) are used to determine the compatibility of the esters in PVC and their potential as replacement for phthalates in qualitative terms. Nothing is said about performance tests or about issues such as migration out of, and susceptibility to evaporation from, the plasticized polymer, or about its long-term service properties.

EP-A 1 873 198 has already disclosed alkyl benzyl esters of aromatic and aliphatic polycarboxylic acids which can be used as plasticizers with low solvation temperature for plastics.

However, the succinic esters mentioned, known from the prior art, do not meet all of the aspects of the desired requirements placed upon a good plasticizer, in particular in relation to plasticizer effectiveness and processibility, and in this regard they remain unsatisfactory.

Starting from the known prior art, the present invention had the object of providing novel plasticizers for plastics based on succinic esters and having improved properties, in particular in relation to plasticizing action in conjunction with improved processibility of the final product.

It has now been found that mixtures of succinic esters based on alkyl and benzyl alcohols have particularly good suitability as plasticizers for plastics, in particular as plasticizers for PVC. Surprisingly, the mixtures of the invention not only have a low solvation temperature but also feature very good plasticizing properties. A low solvation temperature is advantageous because it permits faster processing of the plastics, or processing of the plastics at lower temperatures.

The present invention provides mixtures of succinic esters characterized in that they comprise at least two compounds selected from the formulae

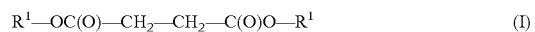

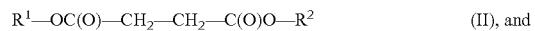

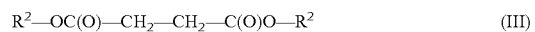

in which
$R^1$ is a straight-chain or branched alkyl moiety, and
$R^2$ is an optionally substituted benzyl moiety.

Preference is given to mixtures of succinic esters where, in the formulae (I), (II), and (III)
$R^1$ is a straight-chain or branched alkyl moiety having from 1 to 12 carbon atoms, and
$R^2$ is an optionally $C_1$-$C_4$-alkyl- or halogen-substituted benzyl moiety.

Particular preference is given to mixtures of succinic esters where, in the formulae (I), and (II),
$R^1$ is a straight-chain or branched alkyl moiety having from 8 to 12 carbon atoms, and
$R^2$ is an optionally $C_1$-$C_4$-alkyl-substituted benzyl moiety.

Very particular preference is given to mixtures of succinic esters where, in the formulae (I), (II), and (III)
$R^1$ is a straight-chain or branched alkyl moiety having 8, 9, 10, or 11 carbon atoms, and
$R^2$ is benzyl ($=CH_2-C_6H_5$).

Examples of straight-chain or branched alkyl moieties that can be used as $R^1$ are: methyl; ethyl; propyl such as n-propyl, isopropyl; butyl such as n-butyl, sec-butyl, isobutyl; amyl; hexyl, such as n-hexyl, 1,4-dimethylbutyl; n-heptyl; octyl such as isooctyl, n-octyl, 2-ethylhexyl; nonyl such as n-nonyl and isononyl; decyl. such as n-decyl, isodecyl; and dodecyl such as n-dodecyl and isododecyl moieties, and all of the various isomeric forms of these.

Examples of optionally substituted benzyl moieties that can be used for $R^2$ are: methylbenzyl, dimethylbenzyl, trimethylbenzyl, ethylbenzyl, isopropylbenzyl and tert butylbenzyl, chlorobenzyl, dichlorobenzyl, trichlorobenzyl, bromobenzyl, and dibromobenzyl moieties.

Particular preference is given to mixtures of alkyl succinates in which, in the formulae (I), (II), and (III), $R^1$ is 2-ethylhexyl-, n-octyl-, isooctyl-, n-nonyl-, isononyl-; 3,5,5-trimethylhexyl-, n-decyl-, isodecyl-; n-dodecyl-, or isododecyl, and $R^2$ is benzyl.

Particular preference is further given to a) mixtures of alkyl succinates characterized in that they comprise the compounds of the formulae (I), (II), and (III). In the mixtures a) the general and preferred definitions of the moieties $R^1$ and $R^2$ are respectively those stated above. Among the mixtures a), very particular preference is in turn given to those in which in the formulae (I), (II), and (III), $R^1$ is 2-ethylhexyl, n-octyl, isooctyl-, n-nonyl, isononyl-; 3,5,5-trimethylhexyl, n-decyl-, isodecyl-; n-dodecyl-, or isododecyl, and $R^2$ is benzyl.

In the mixtures a) the amount of compound of the formula (I) is generally from 10 to 50% by weight, preferably from 15 to 35% by weight, and very particularly preferably from 20 to 30% by weight, the amount of compound of the formula (II) is generally from 25 to 75% by weight, preferably from 35 to 65% by weight, and very particularly preferably from 40 to 60% by weight, and the amount of compound of the formula (III) is generally from 10 to 50% by weight, preferably from 15 to 35% by weight, and very particularly preferably from 20 to 30% by weight, based in each case on 100 percent of the mixture.

Particular preference is likewise given to b) mixtures of alkyl succinates which are characterized in that they comprise the compounds of the formulae (I) and (III). In the mixtures b) the general and preferred definitions of the moieties $R^1$ and $R^2$ are respectively those stated above. Among the mixtures b), very particular preference is in turn given to those in which in the formulae (I), and (III), $R^1$ is 2-ethylhexyl, n-octyl, isooctyl-, n-nonyl-, isononyl-; 3,5,5-trimethylhexyl, n-decyl-, isodecyl-; n-dodecyl-, or isododecyl, and $R^2$ is benzyl.

In the mixtures b) the amount of compound of the formula (I) is generally from 15 to 95% by weight, preferably from 25 to 75% by weight, and very particularly preferably from 40 to 60% by weight, and the amount of compound of the formula (III) is generally from 85 to 5% by weight, preferably from 75 to 25% by weight, and very particularly preferably from 60 to 40% by weight, based in each case on 100 percent of the mixture.

The compounds of the formula (II) are novel and likewise provided by the present invention. Preference is given to those compounds of the formula (II) in which $R^1$ is 2-ethylhexyl, n-octyl, isooctyl-, n-nonyl-, isononyl-; 3,5,5-trimethylhexyl, n-decyl-, isodecyl; n-dodecyl-, or isododecyl, and $R^2$ is benzyl. The compounds (II) have excellent suitability as plasticizers for plastics.

The mixtures of the invention can be produced by various processes: by way of example it is possible to react two different monohydric alcohols of the formulae $R^1$—OH (IV) and $R^2$—OH (V), in which $R^1$ and $R^2$ have the general and preferred definitions stated for the formulae (I) to (III), with succinic acid in a manner known per se with elimination of water. The process can be carried out in a single step or in two steps. If it is carried out in a single step, all of the reactants are in essence simultaneously brought into contact with one another and reacted. In the case of the reaction in two steps, a first step reacts the succinic acid or a derivative thereof with an alcohol and the resultant reaction mixture is reacted with the second alcohol. The reaction mixture can be diluted with a solvent, which can also serve as entrainer for removal of water of reaction. The monohydric alcohols used to form the ester can simultaneously be used as entrainers and in excess. The esterification of the succinic acid can be carried out with or without typical catalysts familiar to the person skilled in the art.

It is also possible to produce the mixtures of the invention by reaction of the alcohols of the formulae (IV) and (V) with succinoyl halides with elimination of hydrophilic acid. The alcohols of the formulae (IV) and (V) here can be reacted either simultaneously or in succession. It is moreover possible to produce the mixture of the invention by transesterification of a succinic ester of short-chain alcohols, for example dimethyl succinate, with the alcohols of the formulae (IV) and (V), with elimination of, for example methanol, or by hydrogenation of the corresponding ester mixture of fumaric or maleic acid. IL is also possible to use benzyl chloride instead of benzyl alcohol for the benzylation reaction. The mixtures of the invention can also be produced in other ways, for example by mixing various amounts of the individual components (I), (II), and (III).

The reactions described above can be followed by purification operations familiar to the person skilled in the art, for example extraction, in particular aqueous wash, steam distillation or other distillation, adsorption, and/or filtration.

The present invention also provides a process for the production of an ester mixture of the invention comprising the compounds of the formulae

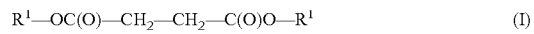 (I)

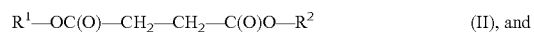 (II), and

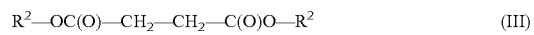 (III)

in which
$R^1$ is a straight-chain or branched alkyl moiety, and
$R^2$ is an optionally substituted benzyl moiety, the process being characterized in that, in a single process step or in two successive process steps, two different monohydric alcohols of the formulae $R^1$—OH (IV), and $R^2$—OH (V), in which the general and preferred definitions of $R^1$ and $R^2$ are those given above for the formulae (I) to (III), are reacted at a temperature of from 50 to 250° C. and optionally at a pressure of from 2 mbar to 4 bar and optionally in the presence of a catalyst with succinic acid, and the resultant water of reaction is removed from the mixture by suitable measures, such as distillation.

Examples of alcohols of the formula (IV) that can be used are: methyl; ethyl; propyl, such as n-propyl, isopropyl; butyl, such as n-butyl, sec-butyl, isobutyl; amyl; hexyl, such as n-hexyl, 1,4-ditnethylbutyl; n-heptyl; octyl, such as isooctyl, n-octyl, 2-ethylhexyl; nonyl, such as n-nonyl and isononyl; decyl, such as n-decyl, isodecyl; and dodecyl, such as n-dodecyl, and isododecyl alcohol and all of the various isomeric forms of these.

Examples of alcohols of the formula (V) that can be used are: benzyl alcohol, and also alkyl-substituted benzyl alcohols, such as methylbenzyl alcohol, ethylbenzyl alcohol, dimethylbenzyl alcohol, trimethylbenzyl alcohol, isopropylbenzyl alcohol, tert-butylbenzyl alcohol, and also halogen-substituted benzyl alcohols, such as chlorobenzyl alcohol, dichlorobenzyl alcohol, trichlombenzyl alcohol, bromobenzyl alcohol, dibromobenzyl alcohol, and the like.

Suitable catalysts are in principle compounds of the formula MXn, in which M is a metal cation selected from the group of the metals titanium, zirconium, vanadium, aluminum, iron, and tin, and X is an anion selected from the group, —$CO_3^{2-}$, $Cl^-$, $Br^-$, $I^-$;, —$OR^-$, where R is selected from methyl, ethyl, n-propyl, isopropyl, n-butyl, isobutyl, t-butyl; carboxylate, in particular hexanoate, heptanoate, octanoate, 2-ethylhexanoate, stearate, palmitate, oxalate; and in which n is the oxidation number of the metal, preferably 2, 3, or 4. It is also possible to use, as a successful alternative, strong Bronsted acids, such as sulfuric acid, acidic sulfates, e.g. methyl sulfate, ethyl sulfate, propyl sulfate, butyl sulfate, hexyl sulfate, or else $KHSO_4$ or $NaHSO_4$, or aromatic sulfonic acids, in particular para-toluenesulfonic acid or benzenesulfonic acid.

The present invention likewise provides a process for the production of an ester mixture of the invention comprising the compounds of the formulae $$R^1-OC(O)-CH_2-CH_2-C(O)O-R^1 \quad (I), \text{ and}$$

$$R^2-OC(O)-CH_2-CH_2-C(O)O-R^2 \quad (III),$$

in which
$R^1$ is a straight-chain or branched alkyl moiety, and
$R^2$ is an optionally substituted benzyl moiety,
which process is characterized in that the individual compounds of the formulae (I) and (II) are mixed with one another.

The present invention likewise provides a process for the production of compounds of the formula $$R^1-OC(O)-CH_2-CH_2-C(O)O-R^2 \quad (II)$$

in which
$R^1$ is a straight-chain or branched alkyl moiety, and
$R^2$ is an optionally substituted benzyl moiety,
which process is characterized in that the compound of the formula (II) is separated from the ester mixture of the formulae (I), (II), and (III), or in a two-stage process acid or anhydride is reacted with the alcohols of the formulae (IV) and (V) or its or synthesis equivalents in succession, in combination with a possible purification step after stage 1 or 2.

If the succinic acid used for the production of the succinic ester mixtures of the invention has been produced from bio-based feedstocks, e.g. by a microbiological fermentation process, the succinic acid can comprise contaminants which in turn can also be found in the mixtures of the invention. Typical contaminants which can pass into the final products by virtue of the microorganisms used are nitrogen- and sulfur-containing compounds.

It is preferable that the ester mixtures of the invention comprise less than 1000 ppm content by mass of nitrogen atoms and less than 50 ppm content by mass of sulfur atoms, based in each case on the mixture. The mixtures of the invention comprise particularly preferably from 0.01 to 750 ppm content by mass of nitrogen atoms and from 0.0001 to 40 ppm content by mass of sulfur atoms, based in each case on the mixture.

The present invention also provides an ester mixture comprising at least two alkyl succinates of the formulae (I), (I), and (III) characterized in that the alkyl succinates of the formulae (I), (II), and (III) derive from biomass resources and the mixture comprises from 0.01 ppm to 1000 ppm content by mass of nitrogen atoms and from 0.01 ppm to 50 ppm content by mass of sulphur atoms, based in each case on the mixture.

These ester mixtures of the invention can be produced by using, in the conduct of the production process of the invention, alcohols of the formulae (IV) and (V) and succinic acid which derive from biomass resources and where the content by mass of nitrogen atoms, based on the total mass of alcohols used and succinic acid, is in the range from 0.01 ppm to 1000 ppm, and the content by mass of sulfur atoms, based on the total mass of alcohols used and succinic acid, is in the range from 0.01 ppm to 50 ppm.

The suitability of the succinic ester mixtures of the invention as plasticizers is not adversely affected by the presence of the small amounts mentioned of typical contaminants.

The novel succinic ester mixtures have excellent suitability as plasticizers for plastics.

The invention further provides the use of a succinic ester mixture of the invention as plasticizer for plastics.

Examples of suitable plastics are polyvinyl chloride (PVC), vinyl-chloride-based copolymers, polyvinylidene chloride, polyvinyl acetals, polyvinyl butyral, polyacrylates, polymethacrylates, polyalkyl methacrylates, such as poly(methyl methacrylate), polyamides, polyurethanes, polylactides, polylactic acids, polyvinyl acetate, cellulose and its derivatives, ethylene-vinyl acetates, rubber polymers, such as acrylonitrile-butadiene rubber, hydrogenated acrylonitrile-butadiene rubber, styrene-butadiene rubber, chloroprene rubber, ethylene-propylene rubber, acrylate rubber, and natural rubber. It is preferable that the succinic ester mixtures of the invention are used as plasticizers and processing aids for PVC and polyacrylates.

When the plastics produced with the novel plasticizers are compared with the plastics known from the prior art, produced with plasticizers based on single-component succinic esters, they are distinguishable by low hardness and high flexibility.

When the use of the plasticizers of the invention is compared with the use of the known and less efficient, symmetrical succinic esters, it is possible to save costs by reducing the amount of plasticizer in order to achieve the same hardness in the final products. The use of less plasticizers, or the reduction of the amount of plasticizer used, also provides better final-product properties in respect of volatility and migration of the plasticizer.

The invention also provides the use of the succinic ester mixtures of the invention as processing aids and plasticizers in adhesives, in components of adhesives, in adhesive sealants, in components of adhesive sealants, in sealing compositions, in components of sealing compositions, or in coating compositions, in paints, inks, or coating materials, or in plastisols, inclusive of PVC-plastisols, and as plasticizers in plastics or in components of plastics, preferably in polyvinyl chloride.

The present invention also provides plasticizer preparations comprising a succinic ester mixture of the invention and optionally other conventional additives. Examples of these additives that can be used are other plasticizers, light stabilizers and other stabilizers, antioxidants, lubricants, fillers, pigments, flame retardants, blowing agents, kickers, polymeric processing aids, impact modifiers, optical brighteners, antistatic agents, and biostabilizers.

Types of PVC that can be used are suspension PVC, bulk PVC, microsuspension PVC, and emulsion PVC. The mixtures here can be used alone or in combination with other plasticizers. The amounts used of the plasticizers of the invention are generally from 10 to 200 parts, preferably from 20 to 150 parts, in each case for every 100 parts of plastic.

The novel plasticizer preparations permit the production of final products with good low-temperature properties. It is preferable that the mixtures of the invention are used for the production of plastisols, preferably of plastisols based on PVC. When the low-viscosity succinic ester mixtures are used in PVC plastisols, they permit production of low-viscosity, storage-stable plastisols.

The plastics produced with use of the plasticizer preparations of the invention, in particular polyvinyl chloride, can also comprise other suitable auxiliaries and additives, alongside the plasticizer preparations of the invention. Examples of these are other plasticizers, light stabilizers and other stabilizers, antioxidants, lubricants, fillers, pigments, flame retardants, blowing agents, kickers, polymeric processing aids, impact modifiers, optical brighteners, antistatic agents, and biostabilizers.

The present invention further provides a process for production of plasticized plastics, in particular of plasticized PVC, which is characterized in that in a first step PVC, in particular emulsion PVC and microsuspension PVC, is mixed at from 10 to 60° C. with the plasticizer preparation of the invention and optionally with other auxiliaries and additives, where from 10 to 200 parts of the plasticizer preparation of the invention are used for every 100 parts of plastic. in a second step, this plastisol is molded and, at temperatures of from 140 to 200° C., processed to give the final product.

Production Examples and Technical Testing

The following examples serve to illustrate the present invention and are in no way intended to be restrictive.

Production of a Succinic Ester Mixture of the Invention

Example 1

177 g of succinic acid 268 g of 2-ethyl-1-hexanol, and 221 g of benzyl alcohol are used as initial charge in 175 ml of xylene in a nitrogen-gas-inertized 1 l multinecked round-bottomed flask with water separator and reflux condenser, internal thermometer, and stirrer. After addition of 0.3 g of tetrabutyl titanate, the mixture was heated to reflux, with stirring, and resultant water of reaction was removed from the system. The course of the reaction was monitored by means of titration [acid number] and water separation. Once an acid number smaller than or equal to 1 had been reached, the reaction was terminated. After modification of the apparatus, xylene and the excess of alcohol were removed by distillation in vacuuo, starting at 20 mbar; the bottom temperature at the end of the distillation process was 190° C. After cooling, the catalyst was washed with water and aqueous sodium carbonate solution. The volatile constituents were then removed by distillation from the organic phase, starting at 120° C. and 20 mbar. and the performance of the mixture as plasticizer was tested. Yield was 435 g (91%). Composition by GC area percent is: 29.8% di(2-ethylhexyl) succinate, 49.7% benzyl-2-ethylhexyl succinate, and 20.3% dibenzyl succinate.

Examples 2-7

By analogy with example 1, other ester mixtures of the invention were produced by reaction of succinic acid with the corresponding alkyl and benzyl alcohols. The results of performance testing for examples 1 to 7 are shown in Table 1.

Performance Testing

Determination of Solvation Temperature:

48.0 g of the substance to be tested were weighed into a glass beaker with magnetic stirrer rod and thermometer. The glass beaker was placed on a magnetic heater-stirrer in a holder between a lamp and a photocell. The change in light transmittance of the sample was recorded by way of a photocell. 2 g of polyvinyl chloride (Vinnolit® S4170; Vinnolit GmbH & Co. KG, Germany), and, by means of a pipette, 2 drops of PVC stabilizer (organotin stabilizer) were then added. The polyvinyl chloride was stirred into the plasticizer and the mixture was heated rapidly at from 5-8° C. per minute to 100° C., with stirring, and then further heated at an average of 3° C. per minute. Solvation temperature was considered to have been reached when for 3 successive minutes no further rise in the transmittance value was recorded by the photocell, and the polyvinyl chloride had been dissolved. Measurement was terminated when the temperature of the contents of the glass beaker reached 200° C. Low solvation temperature indicates good compatibility of the plasticizer and of the plasticizer preparations with polyvinyl chloride and indicates that high-speed processing is possible.

Determination of Hardness:

Hardness was determined by homogenizing and gelling a plasticizer-containing PVC powder mixture on a two-roll mill; the compounded material was then pressed to give test sheets, and hardness was determined by Zwick Shore-hardness equipment. Hardness (Shore A) was measured on smooth and even test samples measuring 6 mm×40 mm×50 mm. Low Shore A hardness values mean relatively soft products and are a measure of the efficiency of the plasticizers.

A rod was used to mix 100 g of polyvinyl chloride (Vinnolit® S4170, Vinnolit GmbH & Co, KG. Germany) with 60 phr (parts per hundred resin) of plasticizer or plasticizer preparation and 3 phr of PVC stabilizer (Ca/Zn carboxylate) in a porcelain dish in such a way that the liquid constituents were absorbed well by the powder, rather than adhering to the vessel. The resultant powder mixture was charged in portions to the nip (07 mm) of a two-roll mill at 165° C. roll temperature, and homogenized and gelled. Once the milled sheet had formed, the nip was widened to 1 mm. The success of the mixing process was improved by frequent turning of the milled sheet. After 10 minutes of mixing time and processing time, the milled sheet was removed. After portioning, test samples measuring 6 mm×40 mm×50 mm were pressed. The temperature of the press was 170° C.; total press time was 10 minutes, including 7 minutes of heating phase with pressure <10 bar and 3 minutes of press time under high pressure >100 bar. After cooling under pressure in a cooling press to at most 30° C., the test samples were demolded. The Shore A hardness of the test samples was determined by Zwick 1-104.3150 equipment in accordance with DIN 53505 at five different locations after, at the earliest, 24 hours of storage at 23° C., and the average value was recorded.

Table 1:

The Shore A hardness of test samples with in each case 60 phr content of plasticizer was determined for the ester mixture of the invention of examples I to 7 and for non-inventive example 7a. Low Shore A hardness value implies good plasticizing capability (efficiency) of the plasticizer. Solvation temperatures were also determined. Solvation temperature serves to indicate the compatibility of a plasticizer with the respective plastics or polymers. Low solvation temperature here indicates good compatibility of the plasticizer with polyvinyl chloride and capability for high-speed processing.

| | Examples | Shore A hardness | Solvation temperature |
|---|---|---|---|
| 1 | Benzyl 2-ethylhexyl succinate mixture | 70 | 134° C. |
| 2 | Benzyl isononyl succinate mixture | 71 | 140° C. |
| 3 | Benzyl 3,5,5-trimethylhexyl succinate mixture | 74 | 147° C. |
| 4 | Benzyl 1-decyl succinate mixture | 73 | 149° C. |
| 5 | Benzyl isodecyl succinate mixture | 72 | 146 |
| 6 | Benzyl isoundecyl succinate mixture | 75 | 155 |
| 7 | Benzyl 1-dodecyl succinate mixture | 93 | 165 |
| 7a | Di-1-dodecyl succinate mixture | no plasticizing action | 196 |

Table 1 shows that the ester mixtures of the invention have good plasticizing properties in combination with low solvation temperature. The ester mixtures of the invention can therefore be used as efficient plasticizers which moreover also permit processing of PVC at low temperatures, and this in turn leads to energy savings and shorter production-cycle times. Surprisingly, therefore, use of the plasticizer mixtures of the invention can give softer products, or a cost-efficient reduction of plasticizer content in products of identical hardness. Lower usage of the potentially migrating or volatile plasticizers permits production of final products with better properties in respect of volatility and migration of the plasticizer. Comparison of example 7 with 7a shows the favorable effect on hardness and solvation temperature due to the benzyl moiety in the benzyl 1-dodecyl succinate mixture of the invention, in comparison with di-1-dodecyl succinate.

What is claimed is:

1. A mixture of succinic esters characterized in that it comprises at least two compounds selected from the formulae $$R^1—OC(O)—CH_2—CH_2—C(O)O—R^1 \quad (I)$$

$$R^1—OC(O)—CH_2—CH_2—C(O)O—R^2 \quad (II), \text{ and}$$

$$R^2—OC(O)—CH_2—CH_2—C(O)O—R^2 \quad (III)$$

in which
$R^1$ is a straight-chain or branched alkyl moiety, and
$R^2$ is an optionally substituted benzyl moiety.

2. The ester mixture as claimed in claim 1, where, in the formulae (I), (II), and (III)
$R^1$ is a straight-chain or branched alkyl moiety having from 1 to 12 carbon atoms, and
$R^2$ is an optionally $C_1$-$C_4$-alkyl- or halogen-substituted benzyl moiety.

3. The ester mixture as claimed in claim 1, characterized in that, in the formulae (I), (II), and (III), $R^1$ is a straight-chain or branched alkyl moiety having from 8 to 12 carbon atoms, and $R^2$ is a benzyl moiety.

4. The ester mixture as claimed in claim 1, characterized in that it comprises the compounds of the formulae (I), (II), and (III).

5. The ester mixture as claimed in claim 4, characterized in that the amount of compound of the formula (I) is from 10 to 50% by weight, the amount of compound of the formula (II) is from 25 to 75% by weight, and the amount of compound of the formula (II) is from 10 to 50% by weight, based in each case on 100 percent of the mixture.

6. The ester mixture as claimed in claim 1, characterized in that it comprises only the compounds (I), and (III).

7. The ester mixture as claimed in claim 6, characterized in that the amount of compound of the formula (I) is from 15 to 95% by weight, and the amount of compound of the formula (III) is from 85 to 5% by weight, based in each case on 100 percent of the mixture.

8. An alkyl succinate of the formula $$R^1—OC(O)—CH_2—CH_2—C(O)O—R^2 \quad (II)$$

in which
$R^1$ is a straight-chain or branched alkyl moiety, and
$R^2$ is an optionally substituted benzyl moiety.

9. The ester mixture as claimed in claim 1, characterized in that the succinic esters of the formulae (I), (II), and (III) derive from biomass resources, and the mixture comprises from 0.01 ppm to 1000 ppm content by mass of nitrogen atoms and from 0.01 ppm to 50 ppm content by mass of sulfur atoms, based in each case on the mixture.

10. A process for the production of an ester mixture as claimed in claim 4, characterized in that in a single process step or in two successive process steps two different monohydric alcohols of the formulae $R^1$—OH (IV), and $R^2$—OH (V), in which $R^1$ is a straight-chain or branched alkyl moiety, and $R^2$ is an optionally substituted benzyl moiety, are reacted at a temperature of from 50 to 250° C. and optionally at a pressure of from 2 mbar to 4 bar and optionally in the presence of a catalyst with succinic acid, and the resultant water of reaction is removed from the mixture by suitable measures.

11. A plasticizer preparation comprising an ester mixture or comprising a succinic ester as claimed in claim 1.

12. A process for production of plasticized plastics, characterized in that in a first step PVC is mixed at from 10 to 50° C. with a plasticizer preparation as claimed in claim 11 and optionally with other auxiliaries and additives, where from 10 to 200 parts of the plasticizer preparation are used for every 100 parts of plastic, and in a second step the resultant plastisol is molded and, at temperatures of from 140 to 200° C., processed to give the final product.

13. A plastisol comprising at least one plastic and one plasticizer preparation as claimed in claim 11.

* * * * *